United States Patent [19]

Hetz

[11] Patent Number: 4,535,781
[45] Date of Patent: Aug. 20, 1985

[54] MANUALLY OPERATED ULTRASOUND APPLICATOR

[75] Inventor: Walter Hetz, Erlangen, Fed. Rep. of Germany

[73] Assignee: Siemens Aktiengesellschaft, Berlin and Munich, Fed. Rep. of Germany

[21] Appl. No.: 487,785

[22] Filed: Apr. 22, 1983

[30] Foreign Application Priority Data

Apr. 26, 1982 [DE] Fed. Rep. of Germany ....... 3215529

[51] Int. Cl.³ .............................................. A61B 10/00
[52] U.S. Cl. .................................................... 128/660
[58] Field of Search ..................... 128/4, 660, 20, 661; 73/633, 634, 620; 33/497, 499, 500, 153 B; 24/537, 241 SL, 652

[56] References Cited

U.S. PATENT DOCUMENTS

| | | | |
|---|---|---|---|
| 4,078,555 | 3/1978 | Takahashi | 128/4 |
| 4,151,834 | 5/1979 | Sato et al. | 128/660 |
| 4,174,715 | 11/1979 | Hasson | 128/321 |
| 4,205,417 | 6/1980 | Mackal | 24/537 |
| 4,206,653 | 6/1980 | LeMay | 73/620 |
| 4,238,865 | 12/1980 | Ingemann et al. | 24/537 |
| 4,305,014 | 12/1981 | Borburgh et al. | 310/334 |
| 4,308,981 | 1/1982 | Miura | 24/537 |
| 4,483,344 | 11/1984 | Atkov et al. | 128/661 |

FOREIGN PATENT DOCUMENTS

| | | | |
|---|---|---|---|
| 0039045 | 4/1981 | European Pat. Off. . | |
| 0039851 | 11/1981 | European Pat. Off. | 128/660 |
| 2924194 | 10/1980 | Fed. Rep. of Germany | 128/660 |
| 2474303 | 7/1981 | France . | |

OTHER PUBLICATIONS

O. Richter and R. V. Voss, *Bauelemente Der Feinmechanik*, Veb Verlag Technik Berlin, 1959, p. 282.

Primary Examiner—Kyle L. Howell
Assistant Examiner—Ruth S. Smith
Attorney, Agent, or Firm—Mark H. Jay

[57] ABSTRACT

An ultrasonic transducer is pivotally attached to one end of an elongated handle which is divided into first and second half shells. The transducer can be freed to rotate or locked in position by moving the half shells apart or together, respectively. The resulting ultrasound applicator is useful for intra-operative scanning.

1 Claim, 8 Drawing Figures

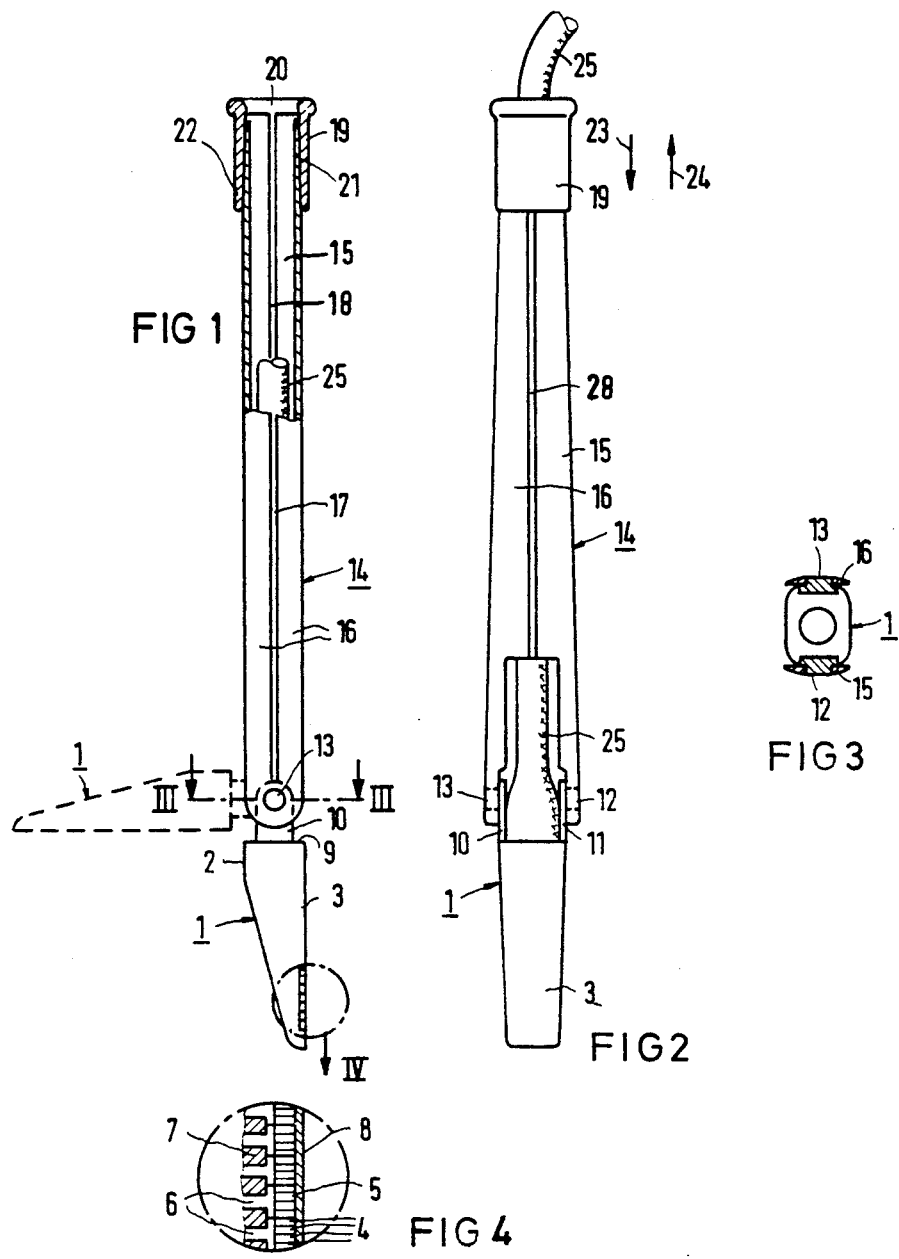

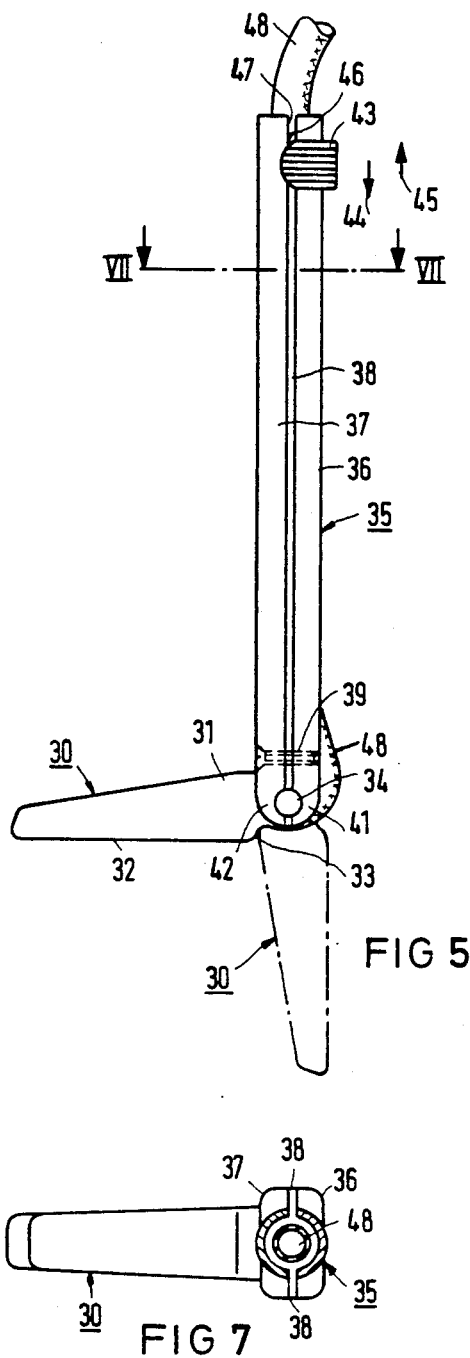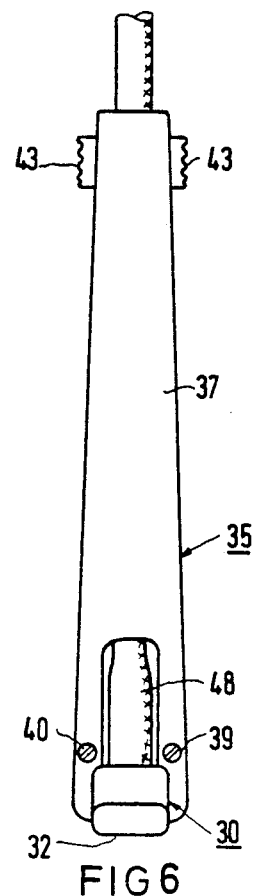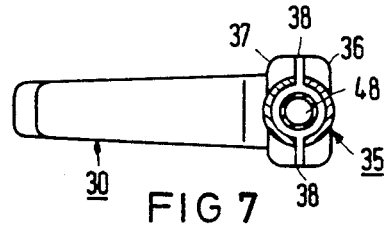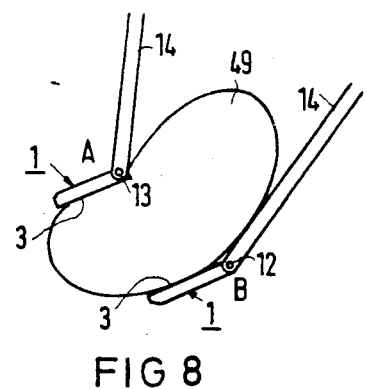

MANUALLY OPERATED ULTRASOUND APPLICATOR

BACKGROUND OF THE INVENTION

The invention relates to an ultrasound applicator for diagnosis; more specifically it relates to a manually operated applicator suitable for examining internal organs and tissues of the human body, which applicator incorporates an ultrasound transducer composed of a plurality of converter elements built into an elongated, rigid housing having a scanning surface designed for placement onto the body area or organ to be examined. The housing, furthermore, is equipped with an elongated handle being connected to the ultrasound transducer by means of a joint member.

Ultrasound applicators of this kind conventionally are designed for scanning internal organs of the human body through the skin, however it would be desirable to provide a ultrasound applicator designed for use during open surgery especially for diagnosis of tissues or organs directly accessible from the outside just during such treatment.

The published German Patent Application No. 2,950,203, discloses an endoscope constituting an eye piece, a flexible tube, including a bendable connecting portion and a cylinder-shaped front portion. A light conductor and control cables are arranged within the flexible tube and the front portion bears a built-in ultrasound transducer. The known endoscope is not very well adapted for use during open surgery because it cannot be sufficiently sterilized due to its sensitive optical system. In addition, the design of the bendable connecting portion renders the known endoscope applicable only for examination procedures requiring just relatively small bending angles. It is also desirable to keep the surgical area i.e. the field of the human body affected by an operation as small as possible and it is difficult to apply the cylinder-shaped endoscope in a manner which places the ultrasound transducer—seen from the perspective of the surgical area—beneath the object of examination. Therefore, possible applications of the known apparatus are rather limited.

European Patent Application No. 0,039,045 discloses another endoscope comprising a remotely controlled bendable front portion and two ultrasound transducers arranged therein. Similar to the mentioned endoscope, again the front portion of this endoscope has a relatively small bending angle which most likely amounts to not more than a few degrees. The manipulation mechanism providing remote control and installed in the endoscope's interior is rather bulky, therefore the endoscope can only be applied to surgical areas of sufficient dimensions.

A medical ultrasound testing probe is disclosed in the specification of German Utility Model No. 6,942,159, incorporating a flexible tube, a handle connected to one end of the flexible tube and an ultrasound converter arranged at the other end. It is not possible to bend the ultrasound converter with respect to the adjacent end of the tube, which limits the use of the testing probe for examinations of internal organs during surgical operation.

SUMMARY OF THE INVENTION

It is, therefore, a main object of the present invention to provide for an improved ultrasound applicator suitable for a variety of applications in open surgery.

It is another object of the present invention to provide for a simple, reliable tool for the surgeon which allows for examining of parts of the human body which until now are physically touched and examined by hand.

It is a further object of the present invention to provide for a manually operated ultrasound applicator having small dimensions suitable for easy handling when utilized in small surgical areas.

It is still another object of the present invention to provide for such an ultrasound applicator designed for being manufactured at reasonable cost without comprising in view of essential characteristics such as easy and controlled handling, reliability and suitability for satisfactory sterilization.

These objects, as well as other objects which will become apparent from the description which follows, are achieved by a manually operated ultrasound applicator for scanning of tissues and internal organs of the human body and incorporating an ultrasound transducer composed of a plurality of converter elements being mounted in an elongated rigid housing. The housing is provided with a scanning surface designed for being placed onto the body area to be examined. The applicator further includes an elongated handle coupled to the ultrasound transducer. In accordance with the present invention such ultrasound applicator incorporates joint means for coupling the transducer to the handle in a pivotal mode, wherein a temporary tilting position of the transducer with respect to the handle can be selected by hand. Furthermore, there are provided means for securing a selected tilted position of the transducer.

Such an ultrasound applicator designed according to the present invention enables safe and reliable adjustment of the ultrasound transducer to a desired examination position by means of an accordingly designed handle. This design allows for a safe placement of the ultrasound transducer onto the surface of the object to be examined. The ultrasound transducer can already be tilted to a chosen angle position when contact is being made with a selected surface area. However, it is conceivable that the securing means are opened which enables a movement of the transducer to a selected area of the object to be examined. In this case the scanning surface of the transducer follows all changes of the object surface without applying undesired force onto the same and the securing means are only activated for providing a secure and reliable scanning operation of the transducer.

This design allows for adjusting the ultrasound transducer in a simple manner by hand to suit any desired tilting position in a wide range of tilting angles. Any desired placement of the ultrasound applicator with respect to internal organs to be examined, at the back, front or side walls of such organ to be scanned is made possible. Therefore, the ultrasound applicator is especially suited for various applications in conjunction with surgical measures. This tool is almost as capable of movement in any direction as a finger of the feeling hand of a surgeon with the extended capability of reliable scientific tool. This renders it possible to make full use of the entire scanning surface, that is to say even examinations at large depths in cavities of the human body are made possible when the open surgical areas are comparatively small.

For a full understanding of the present invention of further advantages and details, reference should now be made to the following description of preferred embodiments in conjunction with the accompanying drawings.

BRIEF DESCRIPTION OF THE DRAWINGS

A better understanding of the invention may be had by reference to the following description of preferred embodiments in conjunction with the accompanying drawings in which:

FIG. 1 is a sideview of a first embodiment of an ultrasound applicator according to the present invention with a handle and a transducer member pivotally attached thereto;

FIG. 2 is a front view of the same ultrasound applicator;

FIG. 3 represents a cross-section of the applicator drawn along line III—III of FIG. 1;

FIG. 4 shows an enlarged partional view of a detail IV of the transducer member illustrated in FIG. 1;

FIG. 5 is a sideview of a second embodiment of an ultrasound applicator according to the present invention;

FIG. 6 illustrates the ultrasound applicator represented in FIG. 5 in a front view;

FIG. 7 depicts a cross-section of the ultrasound applicator taken along line VII—VII; and FIG. 8 represents an application of an ultrasound applicator in accordance with the present invention for intra-operative examination of a kidney.

DETAILED DESCRIPTION OF THE PREFERRED EMBODIMENTS

FIGS. 1 through 4 represent different views, a cross-section and a partial sectional view, respectively of a preferred embodiment of a manually operated ultrasound applicator comprising a transducer member 1 and a handle 14 wherein the transducer member is pivotally arranged with respect to the handle.

The transducer member 1 shown in FIG. 1 in two possible tilted positions includes an ultrasound array mounted in an elongated, rigid housing 2 having a scanning surface 3. Details of this scanning surface are illustrated in a sectional view of FIG. 4 representing an enlarged section designated by reference IV in FIG. 1. The ultrasound array is provided with a plurality of converter elements 4 arranged adjacent to scanning surface 3. These converter elements 4 mounted in the housing 2 are finely segmented. A plurality of adjacent elements, for example, four of these segmented converter elements 4, are grouped together by a common electrical contact to an element group 5. A total of 48 groups may be provided. Contact flags 6 of a contact comb each are used for contacting a respective group 5 and are embedded on a support member 7 also bearing the ultrasound converter elements 4. The support member 7 may be composed of an epoxy resin having particles of oxidized tungsten powder implanted therein. A matching layer 8 for the converter elements forms the bottom surface, i.e. the scanning surface 3 of the housing 2 and may also be made of epoxy resin. The design concept of such an ultrasound transducer array comprising fine segmented converter elements is known to those skilled in the art and is disclosed in more detail in U.S. Pat. No. 4,305,014; further detailed description is therefore deemed not to be necessary. Scanning surface 3 can vary in length depending upon the intended applications.

The transducer member 1 has a first and a second end portion, the latter forming a tapered front end tip. The first end portion is formed of a bearing bracket comprising two prongs 10, 11, respectively projecting spaced apart from each other and in parallel to the longitudinal axis of the transducer member 1.

Each of the two prongs 10, 11 carries a corresponding one of two bearing pins 12 and 13, respectively which commonly form a pivoting axis. In the handle 14 there are provided slots 17 and 18, respectively extending close up to pins 12, 13 and lugs are formed in the handle embracing these pins. Handle 14, in fact, is comprised of two slotted shanks 15, 16 as can be best depicted from FIG. 2. In the sideview represented in FIG. 1, the slot cut into the first shank 15 is identified by 18, while the second shank 16 is provided with slot 17.

Lower end portions of both shanks 15 and 16 form a corresponding one of the mentioned lugs to be mounted on a respective one of the bearing pins 12, 13. The design of the shanks is such that they are spaced apart by respective slots formed by the longitudinal edges. FIG. 2 illustrates one of these slots running in parallel to the center axis of the handle and the same slot is identified by reference numeral 28.

The upper end 20 of the assembled handle 14 bears a sliding sleeve 19 mounted opposite to the pivotal joint comprised of members 10, 11, 12, 13. A slideable mounting of sleeve 19 is achieved by conically tapered shanks in the area of the second end portion 20 especially in the end region 21. The inner surface 22 of sliding sleeve 19—as a counter part—is correspondingly tapered in opposite direction.

A sliding movement of sleeve 19 determines a change of friction in the joint, that is the contact surface between a respective shank lug and the associated prong 10 or 11. Thereby, a selected tilted position of the transducer member 1 is secured, when sleeve 19 is moved along handle end 20 downwards in a direction indicated by arrow 23. Consequently, the slotted ends 20 of handle 14 are pressed together by the wedge type effect resulting from the tapered surfaces. The applied pressure is directed to the lower end of shanks 15 and 16 forcing the same against prongs 10 and 11, respectively. Thus the shank lugs hold the transducer member 1 in the selected tilted position by means of prongs 10, 11. A movement of sleeve 19 in opposite direction, as indicated by arrow 24, unlocks the pivotal joint when pressure on ends 20 of handle 14 decreases. Accordingly, no or only a small amount of friction is applied in the joint. Consequently, the transducer member 1 can be swivelled relative to handle 14. In the embodiment illustrated in FIGS. 1 and 2, a signal connection cord 25 attached to the ultrasound array runs through the hollow handle 14.

FIGS. 5 through 7 illustrate a further preferred embodiment. The ultrasound transducer member is referenced with numeral 30 and is again illustrated in two different positions. It includes an array housing 31 providing a scanning surface 32. The ultrasound array may have the same structure as the one described above in conjunction with FIG. 4. The end portion opposite to the tip of the transducer member 30 forms again a bearing bracket including bearing pins forming a swivel or pivotal joint, only one bearing pin 34 is depicted in FIG. 5. Again, handle 35 is comprised of two shanks forming half shells 36 and 37. In contrast to the embodiment described above in conjunction with FIGS. 1 to 4, shanks of this embodiment do not incorporate longitudinal slots. FIG. 5 illustrates, however, an elastic slot 38 formed of the shape of both shanks 36, 37 which are mounted by means of screws 39 and 40 onto the bearing pin 34. By means of this design, handle 35 embraces the bearing pin 34 with the respective lower end portions of the shanks forming jaws in a tong like manner. This is indicated in FIG. 5 by jaws 41 and 42 resting on bearing pin 34. The center of rotation of the tong is determined by the position of screws 39 and 40 located opposite to the jaws 41, 42 with respect to the bearing pin. A spacer element 43 is provided and slidably arranged to be moveable in the longitudinal direction of slot 38 of handle 35. This spacer element 43 is used for releasing or closing the tongs. If it is moved in the direction of arrow 44, both shanks of the handle are forced apart. Correspondingly, jaws 41 and 42 press onto bearing pin 34 and the transducer member 30 is secured in the given tilting position with respect to the handle 35. If spacer element 43 is moved away from the pivotal joint in the direction of arrow 45, it will eventually lock into a recess 46 arranged at the upper end 47 of handle 35 and fully release the shanks. Consequently, the pressure applied by jaws 41 and 42 onto the bearing pin 34 decreases and the transducer member 30 can be freely turned relative to the handle. Again, a signal connection cord 48 connected to the ultrasound array of transducer member 30 is run through the hollow handle 35.

The shanks of both embodiments are preferably made of stainless steel. This allows for easy cleaning and sterilization prior to intra-operative application, since the handle can be disassembled very easily for this purpose. The transducer housing can be manufactured from stainless steel, as well or made of any other rust-proof material, such as synthetics. Before use, a sterilized insulation cap, i.e. a rubber cap—not shown—is slipped over transducer member and handle.

The described ultrasound applicators are especially suited for intra-operative application, although subcutaneous application is possible as well. The possibility of intra-operative application is illustrated by means of a kidney examination schematically represented in FIG. 7. The kidney exposed during surgical operation is identified by numeral 49. The transducer member 1 when being in examination position A, touches the front wall of the kidney. In examination position B the scanning surface of the ultrasound transducer member faces the back wall of the kidney. Application of the described ultrasound applicators is not restricted to examinations of kidneys, any other internal organ or internal part of the human body can be examined likewise.

There has thus been shown and described a novel ultrasound applicator which fulfills all the objects and advantages sought therefor. Many changes, modifications, variations and other uses and applications of this subject invention will, however, become apparent to those skilled in the art after considering the specification and the accompanying drawings which disclose preferred embodiments thereof. It has been shown that the handle constitutes shanks which can be removed from the ultrasound transducer member. The disassembled handle can be cleaned more easily and sterilized without problems prior to any applications in open surgery. One and the same handle can be used as connective element in cooperation with various ultrasound transducer members. All such changes, modifications, variations and other uses and applications which do not depart from the spirit and scope of the invention are deemed to be covered by the invention which is limited only by the claims which follow.

What is claimed is:

1. A manually operated ultrasound applicator for scanning tissues and internal organs of a living subject, comprising:
    an ultrasound transducer which is mounted in an elongated transducer housing having a scanning surface for placement on a region to be scanned and a bearing bracket mounted to an end thereof and projecting horizontally outwardly therefrom;
    an elongated handle, said handle being divided into first and second half shells separated by an elongated slot;
    a bearing pin pivotally connecting the bearing bracket to a first end of the handle, said pin being embraced between said half shells and being rotatable therebetween, whereby the housing is pivotable with respect to the handle;
    at least one screw extending transversely between said half shells adjacent said bearing pin to create a center of rotation of the handle and to thereby cause said half shells at said first end to act as jaws; and
    a sleeve means slidably mounted on the handle on that side of the center of rotation which is opposed to said first end, said sleeve bearing against the half shells to force them apart and thereby change the spacing between the half shells as a function of its position on the handle, permitting the housing to be locked in position with respect to the handle.

* * * * *